United States Patent [19]

Gerrish et al.

[11] Patent Number: 5,688,923
[45] Date of Patent: Nov. 18, 1997

[54] PECTIN FIBERS

[75] Inventors: Timothy C. Gerrish, Kennett Square, Pa.; Gary A. Luzio, Newark, Del.

[73] Assignee: Hercules Incorporated, Wilmington, Del.

[21] Appl. No.: 602,166

[22] Filed: Feb. 15, 1996

[51] Int. Cl.$^6$ .................. A61F 13/00; B01D 21/00; C08B 37/06; C13D 3/00

[52] U.S. Cl. .................. 536/2; 127/29; 602/41; 602/42; 602/45; 602/48; 602/52

[58] Field of Search .................. 536/2; 127/12, 127/29; 602/41, 42, 45, 48, 52

[56] References Cited

U.S. PATENT DOCUMENTS

| | | | |
|---|---|---|---|
| 2,132,065 | 10/1938 | Wilson | 99/132 |
| 4,336,299 | 6/1982 | Holst et al. | 428/288 |
| 4,421,583 | 12/1983 | Aldred et al. | 156/167 |
| 4,562,110 | 12/1985 | Tong | 428/284 |
| 4,614,794 | 9/1986 | Eastern et al. | 530/356 |
| 4,744,830 | 5/1988 | Kobayashi et al. | 106/205 |
| 4,948,575 | 8/1990 | Cole et al. | 424/44 |
| 5,080,657 | 1/1992 | Lee et al. | 604/364 |
| 5,166,231 | 11/1992 | Lee et al. | 524/28 |
| 5,186,936 | 2/1993 | Groves | 424/426 |
| 5,230,853 | 7/1993 | Colegrove et al. | 264/186 |
| 5,290,559 | 3/1994 | Groves | 424/435 |
| 5,470,576 | 11/1995 | Patel | 424/445 |

FOREIGN PATENT DOCUMENTS

| | | |
|---|---|---|
| 0 232 121 A2 | 8/1987 | European Pat. Off. . |
| 0 454 358 A2 | 10/1991 | European Pat. Off. . |
| 0 507 604 A2 | 10/1992 | European Pat. Off. . |
| 4082918 | 3/1992 | Japan . |
| 4082918A | 3/1992 | Japan . |
| 4082919 | 3/1992 | Japan . |
| 40119121 | 4/1992 | Japan . |
| 568177 | 3/1945 | United Kingdom . |

*Primary Examiner*—Nathan M. Nutter
*Attorney, Agent, or Firm*—David Edwards

[57] ABSTRACT

A polyvalent cation crosslinked pectin fiber composition is composed of a calcium sensitive low methoxyl pectin with a degree of esterification (DE) of less than 15% or calcium sensitive amidated pectin having a DE of less than 50% where the pectin is polyvalent cation crosslinkable and has an average molecular weight (MW) having an upper limit of 200,000 and a lower limit of 5000. This pectin is useful in making wound dressings for topical applications.

65 Claims, No Drawings

PECTIN FIBERS

FIELD OF INVENTION

The present invention relates to pectin fibers and a process for spinning them.

BACKGROUND OF THE ART

Prior to the present invention, there were no known commercial processes for making pectin fibers or a commercially available pectin fiber on the market. The only commercially known uronic acid based polysaccharide fiber is alginate fiber.

Prior to the present invention, it was initially observed that pectin fibers were difficult to form and the fibers which were produced were hard and brittle, with low tensile strength. Notwithstanding the above, pectins as a component are known to be incorporated into hydrocolloid type dressings for their beneficial side effects, but pectins used for fibers for wound management have not been previously described as far as can be found in the literature. Consequently, a process for spinning of pectin fibers has not been described.

However, Japanese Kokai Patent Applications No. Hei 4[1992]-82918 (Mar. 16, 1992), No. Hei 4[1994]-82919 (Mar. 16, 1992) and No. Hei 4[1992]-119121 (Apr. 2, 1992) describe extrusion of potassium carrageenan solution into an alcoholic bath or potassium chloride solution. Pectin is listed as a natural water-soluble polysaccharide that can also be used with calcium chloride in this invention.

References to pectin as a modifier have been described in several patents involving fibers. U.S. Pat. No. 4,336,299 (Jun. 22, 1982) describes bonded non-woven fabric. Pectins are mentioned as a modifying agent but fibers are composed of cellulose hydrate and not pectin.

European Patent Application Serial No. 0 454 358 A2 (Oct. 30, 1991) describes melt spinning of a gelling polysaccharide such as gellan or carrageenan. Pectin is mentioned as a non-gelling gum and as an additive but fiber formation is not dependent on the use of pectin. Fiber formation is achieved through thermosetting of a gelling polysaccharide, such as carrageenan; and pectin fiber synthesis is not described or noted.

Hence, a need still exists in the industry for a simple and reproducible process for making pectin fibers that have properties suitable for use in wound dressing applications; those properties include high tensile strength, softness, stability in a wound environment, non-brittleness, sterilizability, fine denier, high level of wet strength, and resilience.

SUMMARY OF THE INVENTION

The present invention relates to a polyvalent cation crosslinked pectin fiber composition comprising an amidated calcium sensitive pectin having a degree of esterification (DE) of less than 50%, or a polyvalent cation crosslinkable low methoxyl pectin having a degree of esterification (DE) of less than 15%. These pectins are further defined by average molecular weight (MW) having an upper limit of 200,000 and a lower limit of 5000. The pectin fibers of the present invention exhibit the measured properties of dry tensile strength of greater than 5 kg/mm$^2$, a wet tensile strength of greater than 0.1 kg/mm$^2$, a preferred dry average diameter of less than 100 micrometers and fiber stability in a solution of 1 percent sodium citrate.

The present invention also is directed to a process for making a polyvalent cation crosslinked pectin fiber composition comprising a) dissolving in water either a low methoxyl calcium sensitive pectin having a DE of less than 15% or an amidated calcium sensitive pectin having a DE of less than 50%, where each pectin has a molecular weight with an upper limit of 200,000 and a lower limit of 5,000;

b) passing the dissolved pectin through a spinneret into a polyvalent cation coagulation bath comprising water and a polyvalent cation, where the polyvalent cation concentration in the bath is set either at a sufficiently high level such that the density of the polyvalent cation solution bath is significantly greater than the density of the pectin solution so that the pectin fibers formed float to top of the bath, or at a sufficiently low level such that the density of the polyvalent cation solution bath is significantly lesser than the density of the pectin solution so that the pectin fibers formed sink to the bottom of the bath; and c) removing the wet pectin fibers, either from the top or bottom of the coagulation bath depending on the density of the bath and drying the pectin fibers. Optionally, the wet pectin fibers are dipped in an alcoholic bath before drying to assist in removal of water. Also, the fiber can be drawn prior to dipping in the alcoholic bath in order to improve tensile strength.

The spun pectin fibers are soft and resilient fibers and can be used in medical applications such as wound care.

DETAILED DESCRIPTION OF THE INVENTION

It has been discovered that it is possible to control the extent of brittleness and to increase the softness and tenacity of a pectin fiber by controlling the amount and the type of side groups present on the pectin molecules and thereby modify the extent of reaction with calcium. This invention makes use of well known facts that pectins can be produced with different degrees of esterification and with random and block de-esterification during processing. In addition amidated groups can be introduced during processing as well. Both the introduction of ester groups and/or amide groups can control the extent of crosslinking in the pectin by a polyvalent cation such as calcium and will result in modification of fiber properties to produce softer fibers with high levels of tensile strength.

In accordance with the invention, only particular types of pectins are useful for the synthesis of pectin fibers which have a high level of tensile strength combined with a soft hand feel. In particular, calcium sensitive amidated pectins or calcium sensitive low methoxyl pectins having a DE of less than 15% are useful for fiber spinning to produce fibers with these desirable properties. The pectins used in this invention are normally derived from citrus fruits such as lime, lemon, grapefruit, and orange, with lemon and lime peel pectin being the preferred.

As used herein, "calcium sensitivity" is intended to mean that property of a pectin product related to an increase in the viscosity of a solution of the pectin product under appropriate conditions using the procedure as described herein below. Since calcium sensitivity is a strong indicator of sensitivity to other cations, the present invention covers sensitivity to such other cations also.

Calcium sensitive pectins can be detected using a calcium sensitivity test whereby calcium ions are added to a pectin solution at low pH preventing reaction between calcium and pectin. The reaction is induced by addition of a buffer solution increasing the pH. The increase in viscosity in the presence of calcium ions compared to the viscosity without calcium is a measure of Calcium Sensitivity (CS).

As used herein, "degree of esterification" is intended to mean the extent to which free carboxylic acid groups contained in the polygalacturonic acid chain have esterified (e.g., by methylation); and "degree of amidation" (DA) is intended to mean the extent to which ester groups contained in the polygalacturonic acid chain have been converted to amide groups when reacted with ammonium hydroxide in solution.

In accordance with the present invention, for calcium sensitive amidated pectins, the DE has an upper limit of 50%, preferably 30%. The lower limit of the DE for the CS amidated pectins are zero (0), preferably 5%, and more preferably 10%. The CS amidated pectins should have an upper limit of the DA of 40%, preferably 25%, and more preferably 20%. The lower limit of the DA is zero (0), preferably 5%, and more preferably 10%.

As noted, it is essential for fiber spinning that the amidated pectins have a high degree of calcium sensitivity and be reactive in the presence of calcium ion to form stable gels. The purity of pectin is measured as anhydrogalacturonic acid (AGA) value. A pure unstandardized pectin normally has an AGA value of greater than 50%.

In accordance with this invention, particular types of low methoxyl pectins that are calcium sensitive can also be used in this invention. Typically in the art, low methoxyl (LM) pectins are defined as pectins with a DE of less than 50%. What is meant by low methoxyl (LM) pectins in the present invention are pectins with DE having an upper limit of less than 15%, preferably less than 10%, more preferably less than 5%. The lower limit of these LM pectins are zero. It has been found that with low methoxyl pectins that compositions containing less than 5% methoxyl content provide the highest levels of tenacity while still providing a soft hand feel. As with amidated pectins it is important than these low methoxyl pectins can react with calcium to form a stable gel.

In accordance with the present invention, the average molecular weight (as determined by viscosity method) of both the amidated pectins and LM pectins has an upper limit of 200,000 daltons, preferably 140,000 daltons, and more preferably 85,000 daltons. The lower limit of the average molecular weight of these pectins is 5,000 daltons, more preferably 20,000 daltons, and most preferably 30,000 daltons. These low average molecular weights of the pectins are desirable to minimize the viscosity for ease of spinning, to obtain a high level of wet strength in the fiber during spinning, and to retain high tensile strength in the dry fiber. Very low molecular weight calcium sensitive pectins of less than 20,000 daltons can result in fibers with low wet tensile strength during spinning, whereas high molecular weight calcium sensitive pectins of greater than 140,000 daltons can form highly viscous solutions which can be difficult to spin through spinnerets that have a small orifice by creating a high back pressure.

In the present invention, other non-pectin polysaccharides can also be blended into the pectin composition prior to spinning. These polysaccharides can be incorporated to modify fiber properties or wound healing properties. These polysaccharides could also have anionic functional groups and can be reactive to calcium or other divalent or polyvalent cations. Polysaccharides which are useful in this manner, include for example, carboxymethyl cellulose, carboxymethyl hydroxyethyl cellulose, sodium alginate, alginic acid, carrageenan, hyaluronic acid, and gellan gum. Any amounts of the other polysaccharides can be present in the blend as long as a sufficient amount of the CS pectin is present to crosslink with the polyvalent cation.

The process of the present invention is simple yet efficient that depends not only on the pectins but also on relative densities in the coagulation bath for its efficient and consistent operation. The pectin solutions are prepared by dissolving calcium sensitive pectins, which contain less than 100 mg of calcium per gram of pectin, in water at temperatures ranging from 50° to 80° C. and then cooling to room temperature. The concentration of the pectin is between 0.5 percent and 10 percent on a weight per unit volume (W/V) basis. The preferred range of concentration is from 2 to 7 percent w/v. The pH of the solution can vary from pH 1 to 9, but for some partially esterified pectins which are unstable under alkaline conditions the preferred range is pH 4 to 6.

This step of the process is followed by filtration through a 5 micron filter in combination with centrifugation to remove undissolved particles to aid in spinning and to prevent clogging of the spinneret. Following filtration, the solution of calcium sensitive pectin is pumped through a spinneret into a spinning solution of calcium chloride at a pressure of between 1 and 20 psi. The pump pressure or flow rate will vary depending on the viscosity of the pectin solution, reactivity to calcium, and hole size of the spinneret. Preferred pressures used range from 5 to 14 psi. The preferred temperature of spinning is between 20° and 300° C. but spinning is not limited to that temperature range. The hole size of the spinneret can range from 20 to 500 microns in diameter but is not limited to this range. The preferred range for hole size is from 50 to 250 microns in diameter. Spinnerets with single or multiple holes can be used.

The pH of the coagulation solution can vary from 1 to 9 depending on the type of pectin used. For amidated pectins the preferred pH range is from 4 to 6. For low DE pectins the range can be from pH 1 to 9 with the preferred range from pH 4 to 6 to produce fibers with high tensile strength. To produce fibers with a soft silky hand feel the preferred range is from pH 1 to 4 with the most preferred range being from pH 2 to 3.

In accordance with this invention, the aqueous spinning solution contains calcium chloride at a concentration of 0.1 to 75 percent calcium chloride at ambient temperature. The preferred range of concentration for the calcium chloride in aqueous solution is from 5 to 40 percent w/v, with the most preferred range being from 15 to 35 percent w/v calcium chloride.

In this aqueous spinning embodiment, the calcium chloride concentration is set at a sufficiently high level such that the density of the calcium chloride solution is significantly greater than the density of the pectin solution. By locating the spinneret at the bottom of the tank with the spinneret holes on the top side of the spinneret, the fibers are formed at the bottom of the tank and are drawn upward towards the top of the tank due to lower density of the fibers relative to the calcium chloride solution. In this manner, the movement of the wet fibers away from the spinneret (due to the positive buoyancy of the fiber) facilitates the continuous formation of new fibers. In this configuration it is preferred that the concentration of the calcium chloride be at least 5 percent w/v to maintain a high level of buoyancy of the fibers. In addition the high concentration of calcium ion accelerates the reaction rate for fiber formation and obviates the need of non-aqueous solvents to aid in fiber formation by precipitation of the polysaccharide as it exits the spinneret.

In accordance with this invention, it should be understood that other types of spinning processes can be used with solutions of calcium sensitive pectins. The wet spinning process described above which avoids the use of organic solvents during spinning is preferred. Nevertheless, the spinning of pectins which are sensitive to calcium ion is not limited to an aqueous wet spinning process. Other types of processes can be used such as solvent spinning in baths of 50% isopropyl alcohol and 50% water containing calcium chloride or dry spinning where the pectin solution is gelled as it exits the spinneret by coinjection of calcium chloride solution into the pectin solution at the exiting point of the spinneret. Gelation and fiber formation takes place in air (as opposed to in solution) in the dry spinning process.

In this solvent spinning process, in baths of 50% isopropyl alcohol (IPA) and 50% water, lower concentrations of calcium chloride are used. In the preferred embodiment the calcium chloride concentration is set at a sufficiently low level such that the density of the calcium chloride/IPA/water solution is significantly less than the density of the pectin solution. By locating the spinneret at the top of the tank with the spinneret holes on the bottom side of the spinneret, the fibers that are formed at the top of the tank are drawn downwardly towards the bottom of the tank because of a higher density of the fibers relative to the calcium chloride/IPA/water solution. In this manner, the movement of the wet fibers downwardly away from the spinneret due to negative buoyancy of the fibers facilitates the continuous formation of new fibers. In this configuration it is preferred that the concentration of the calcium chloride be less than 5 percent w/v and the concentration of IPA be at least 25 percent v/v to maintain a relatively low density in the spinning solution.

In this solvent spinning process the presence of the non-aqueous solvent such as IPA facilitates the formation of a fiber via solvent precipitation of the polysaccharide. Reaction with calcium completes the fiber formation as it exits the spinneret. In the same manner as described above the fibers can be rinsed to remove excess salts and unreacted material. A final rinsing in a water-miscible non-aqueous solvent such as isopropyl alcohol facilitates drying. Drying can be achieved using the same process as described above.

Other readily soluble calcium salts may be used, such as calcium propionate, calcium nitrate, calcium iodide, calcium bromide, or any calcium salt which is soluble in an aqueous solution.

In accordance with the present invention, the polyvalent cations may be selected from a metal ion derived from salts of alkaline earth metal salts, alkali metal salts, transition metal salts, and mixtures thereof. Examples of such polyvalent cations that may be used during the spinning process are salts of aluminum, barium, magnesium, ferric, ferrous, copper, strontium, zinc, or mixtures thereof, but the preferred salts contain calcium ion.

In accordance with this invention, it is possible to use a blend or mixture of salts including monovalent cations as long as at least one salt in the mixture is a divalent or polyvalent cation. Two examples of mixtures of salts are calcium chloride combined with sodium chloride or aluminum chloride combined with calcium nitrate. Any amount of the monovalent cation salt can be used in the blend as long as a sufficient amount of the di- or polyvalent cation is present to crosslink with the CS pectin.

Following spinning, the fiber is washed with water or water/alcohol mixtures to remove excess calcium chloride. The preferred bath is a water bath. Several baths in series may be used to remove excess salt and unreacted material. At this stage, the fiber may be wet drawn to improve tensile strength and to reduce denier.

Following the aqueous washing, the fibers optionally may be rinsed with a non-aqueous water-miscible solvent such as isopropyl alcohol or acetone to facilitate water removal and drying. Drying of the pectin fibers may be performed using conventional techniques; for example, the fibers may be dried in an oven set at a temperature near or above the boiling point of the non-aqueous solvent or may be air dried by blowing air across the fibers or may be dried under a vacuum at elevated temperatures. It is important during the drying stage that the temperature be less than that which could damage the fibers. The drying temperature used will depend on the type of pectin used and the type of gelling salt. In most instances, the drying temperature should not exceed 120° C.

The pectin fibers of this invention can be used in wound dressing compositions for topical medical applications to various types of wounds. This wound dressing can be one or several layers of a gauze material that are either loosely woven or non-woven prepared from the pectin fibers of the present invention. The wound dressing can have a barrier layer with or without adhesives for attaching itself to the wound. These pectin fibers can also be used in wound dressings without a barrier layer. Certain wounds need plenty of air to circulate through a dressing for healing purposes and therefore the wound dressing will not use a barrier layer. Wound dressings are normally sterile and are kept under antiseptic conditions. Wound dressing can have medications impregnated in it that are well known in the art. More specifically, can be either incorporated directly into the pectin fiber itself during the manufacture of the pectin fiber or can be merely added to the wound dressing.

The present invention is further illustrated by the following non-limiting examples wherein all percentages are by weight unless otherwise specified. All of the pectins used in the examples were obtained from Copenhagen Pectin A/S, a division of Hercules Incorporated.

EXAMPLE 1

A wet spinning method was illustrated in 30% calcium chloride by this example. Spinning conditions were as follows:

Flow rate 22.1 ml/hour
Diameter of nozzle 252 micrometers
Length of nozzle 1 cm
Coagulation bath 30 percent w/v calcium chloride
Pectin concentration 2 percent w/v
Pectin type Amidated 104 ASZ; MW=133,000, DE=29%, DA=17.8%, AGA=69.6%

Pectin was dissolved in deionized (DI) water at 80° C. to form a solution, centrifuged at 8,000 rpm and filtered through a 5 micron filter. Using a syringe pump, this filtered solution was pumped at a flow rate of 22.1 ml/hr through a nozzle into a coagulation bath containing 30% of calcium chloride. The nozzle was located at the bottom of the bath with the opening of the nozzle pointed toward the top of the bath. Fibers that were formed were removed from the top of the bath and had a wet tensile strength of 1.1 kg/mm$^2$. The wet fibers were rinsed first in DI water and then isopropyl alcohol; the fibers were then dried overnight under vacuum.

The soft white pectin fibers produced after drying had an average diameter of about 44 micrometers and tensile strengths of 28.0 kg/mm$^2$. Since a relatively high concentration of calcium chloride was used to induce rapid fiber formation, a solvent was not needed or used in this example to aid in phase separation of the pectin from solution.

This example demonstrated that the use of solvents during the spinning process (not necessarily the drying process) can be avoided.

EXAMPLE 2

The process and conditions used in this example were the same as the ones used in Example 1, except that the pectin used in this example was type X4967 which is a low DE amidated pectin; MW=164,000, DE=25%, DA=7.0%, Free Acid Content=68%, AGA=57.1%

The dry fibers produced in this example had diameters of 61 micrometers and average dry tensile strengths of 14.7 kg/mm$^2$. Before drying the fibers, the wet tensile strength was 1.2 kg/mm$^2$.

EXAMPLE 3

A wet spinning method was illustrated in 30% calcium chloride in this example. Spinning conditions were as follows:

Flow rate 5.0 ml/hour

Diameter of nozzle 101 micrometers

Length of nozzle 1 cm

Coagulation bath 30 percent w/v calcium chloride

Pectin concentration 3 percent w/v

Pectin type Low DE LM1912 CSZ; MW=71,100, DE=<5%, DA=0.0%, AGA=72.3%

Pectin was dissolved in deionized (DI) water at 80° C. to form a solution, centrifuged at 8,000 rpm and filtered through a 5 micron filter. Using a syringe pump, this filtered solution was pumped at a flow rate of 5.0 ml/hr through a nozzle into a coagulation bath containing 30% of calcium chloride (at pH5.8). The nozzle was located at the bottom of the bath with the opening of the nozzle pointed toward the top of the bath. Fibers that were formed had a wet tensile strength of 16 kg/mm$^2$. The wet fibers were rinsed first in DI water and then isopropyl alcohol; the fibers were then dried overnight under vacuum.

The soft white pectin fibers produced after drying had an average diameter of about 19 micrometers and tensile strengths of 63.0 kg/mm$^2$. This example demonstrated that fine denier soft fibers could be spun while maintaining a high level of tensile strength.

EXAMPLE 4

The process and conditions used in this example were the same as the ones used in Example 3, except that the pH of the calcium chloride coagulation bath was 2.5. The pectin used was also LM1912 CSZ.

The dry fibers produced in this example had diameters of 19 micrometers and average dry tensile strengths of 52 kg/mm$^2$. These fibers had a silky sheen and hand feel while maintaining a high level of dry strength.

EXAMPLE 5

The process and conditions used in this example were the same as the ones used in Example 3, except the spinning solution was a blend of pectin and alginate. The pectin was LM1912 ASZ at 1.5 percent and the sodium alginate was Protonol HF 60 at 1.5 percent.

The soft dry fibers produced in this example had diameters and tensile strengths comparable to those obtained in example 3. This example demonstrates that other polysaccharides such as alginates can be incorporated into the pectin fiber.

EXAMPLE 6

The process and conditions used in this example were the same as the ones used in Example 3, except the spinning solution was a blend of pectin and hyaluronic acid. The pectin was LM1912 ASZ at 2.25 percent and the hyaluronic acid was at 0.25 percent.

The soft dry fibers produced in this example had diameters and tensile strengths comparable to those obtained in Example 3. This example demonstrates that other polysaccharides such as hyaluronic acid can be incorporated into the pectin fiber.

EXAMPLE 7

A wet spinning method is illustrated using a low MW pectin. Spinning conditions are as follows:

Flow rate—5.0 ml/hour

Diameter of nozzle—250 micrometers

Length of nozzle—1 cm

Coagulation bath—30 percent w/v calcium chloride

Pectin concentration—6 percent w/v

Pectin type—Low DE Type X2952, marketed under the trademark Slendid® 400; MW=22500, DE=<1%, DA=0.0%, AGA=77.5%

Pectin was dissolved in deionized water at 80° C. to form a solution, centrifuged at 8,000 rpm and filtered through a 5 micron filter. Using a syringe pump, this filtered solution was pumped at a flow rate of 5.0 ml/hr through a nozzle into a coagulation bath containing 30% of calcium chloride. The nozzle was located at the bottom of the bath with the opening of the nozzle pointed toward the top of the bath. The wet fibers were rinsed first in DI water and then isopropyl alcohol; the fibers were then dried overnight under vacuum. The soft white pectin fibers produced after drying had an average diameter of about 90 micrometers and tensile strengths of 28.3 kg/mm$^2$. This example demonstrated that fibers could be spun at relatively high concentrations using a low MW pectin while maintaining an acceptable level of tensile strength.

COMPARATIVE EXAMPLE A

The process and conditions used in this example were the same as the ones used in Example 1, except that the pectin used in this example was LM 12CG which is a low DE pectin without amidation; MW=75,000, DE=33.8%, DA=0.0%, Free Acid Content=66.2%, AGA=78.6%

The weak dry fibers produced in this example had diameters of 125 micrometers and a low dry tensile strengths of 4.25 kg/mm$^2$. Before drying the fibers, the wet tensile strength was low at 0.65 kg/mm$^2$. This shows that low methoxyl pectins with DE's greater than 15 percent do not produce acceptable fibers.

COMPARATIVE EXAMPLE B

The process and conditions used in this example were the same as the ones used in Example 1, except that the pectin used in this example was Genu pectin type X2961 which is a partially de-esterified pectin without amidation; MW=116,000, DE=55.9%, DA=0.0%, Free Acid Content=44.1%, AGA=84.3%.

This pectin is not calcium sensitive. A pectin fiber was not produced in this example.

What is claimed:

1. A polyvalent cation crosslinked pectin fiber composition comprising a calcium sensitive low methoxyl pectin with a degree of esterification (DE) of less than 15% or calcium sensitive amidated pectin having a DE of less than 50% where the pectin is polyvalent cation crosslinkable and has an average molecular weight (MW) having an upper limit of 200,000 and a lower limit of 5000.

2. The composition of claim 1 wherein the fiber composition has a dry tensile strength of greater than 5 kg/mm$^2$.

3. The composition of claim 2 wherein the fiber composition has a wet tensile strength of greater than 0.1 kg/mm$^2$.

4. The composition of claim 3 wherein the fiber composition has a fiber diameter of less than 100 micrometers.

5. The composition of claim 4 wherein the fiber composition has a stability in a sodium citrate solution of 1 percent concentration.

6. The composition of claim 1 wherein non-pectin polysaccharides are added to the pectin composition.

7. The composition of claim 6 wherein the polysaccharide is selected from the group consisting of carboxy methyl cellulose, carboxy methyl hydroxy ethyl cellulose, hyaluronic acid, carrageenan, alginic acid, sodium alginate, and gellan gum.

8. The composition of claim 1 wherein the polyvalent cation is selected from a metal ion derived from salts selected from the group consisting of alkaline earth metal salts, alkali metal salts, transition metal salts, and mixtures thereof.

9. The composition of claim 8 wherein the polyvalent cation is selected from the group consisting of calcium, barium, magnesium, zinc, iron, aluminum, copper, strontium, manganese, and mixtures thereof.

10. The composition of claim 9 wherein the cation is selected from the group consisting of calcium, barium, copper, zinc, and iron and aluminum and mixtures thereof.

11. The composition of claim 10 wherein the cation is calcium.

12. The composition of claim 1, wherein the upper limit of the MW is 140,000.

13. The composition of claim 1, wherein the upper limit of the MW is 85,000.

14. The composition of claim 1, wherein the lower limit of the MW is 20,000.

15. The composition of claim 1, wherein the lower limit of the MW is 30,000.

16. The composition of claim 1, wherein the upper limit of the DE of the calcium sensitive amidated pectin is 50%.

17. The composition of claim 1, wherein the upper limit of the DE of the calcium sensitive amidated pectin is 30%.

18. The composition of claim 1, wherein the lower limit of the DE of the calcium sensitive amidated pectin is 0%.

19. The composition of claim 1, wherein the lower limit of the DE of the calcium sensitive amidated pectin is 5%.

20. The composition of claim 1, wherein the lower limit of the DE of the calcium sensitive amidated pectin is 10%.

21. The composition of claim 1, wherein the upper limit of the degree if amidation (DA) of the calcium sensitive amidated pectin is 40%.

22. The composition of claim 1 wherein the upper limit of the DA of the calcium sensitive amidated pectin is 25%.

23. The composition of claim 1 wherein the upper limit of the DA of the calcium sensitive amidated pectin is 20%.

24. The composition of claim 1 wherein the lower limit of the DA of the calcium sensitive amidated pectin is 0%.

25. The composition of claim 1 wherein the lower limit of the DA of the calcium sensitive amidated pectin is 5%.

26. The composition of claim 1 wherein the lower limit of the DA of the calcium sensitive amidated pectin is 10%.

27. The composition of claim 1, wherein the calcium sensitive pectin is derived from citrus pectin.

28. The composition of claim 27, wherein the citrus pectin is selected from the group consisting of lime, lemon, grapefruit, and orange.

29. A process for making a polyvalent cation crosslinked pectin fiber composition comprising
   a) dissolving in water either a low methoxyl calcium sensitive pectin having a DE of less than 15% or an amidated calcium sensitive pectin having a DE of less than 50% and each pectin has a molecular weight with an upper limit of 200,000 and a lower limit of 5,000;
   b) passing the dissolved pectin through a spinneret into a polyvalent cation coagulation bath comprising water and a polyvalent cation, where the polyvalent cation concentration in the bath is set at either a sufficiently high level such that the density of the polyvalent cation solution bath is significantly greater than the density of the pectin solution so that the pectin fibers formed float to top of the bath, or at a sufficiently low level such that the density of the polyvalent cation solution both is significantly lesser than the density of the pectin solution so that the pectin fibers formed sink to the bottom of the bath; and
   c) removing the wet pectin fiber, either from the top or bottom of the coagulation bath depending on the density of the bath and drying the pectin fibers.

30. The process of claim 29, wherein the wet pectin fiber is dipped in an alcoholic bath before drying to assist in removal of water.

31. The process of claim 30, wherein the wet pectin fiber is drawn prior to dipping in the alcoholic bath in order to improve tensile strength.

32. The process of claim 31, wherein the alcohol is selected from the group consisting of isopropyl alcohol, ethanol, propanol, butanol, or any alcohol which is miscible with water.

33. The process of claim 29 wherein the polyvalent cation is selected from a metal ion derived from salts selected from the group consisting of alkaline earth metal salts, alkali metal salts, transition metal salts, and mixtures thereof.

34. The process of claim 33 wherein the cation is selected from the group consisting of calcium, barium, copper, magnesium, iron, zinc, aluminum, manganese, strontium and mixtures thereof.

35. The process of claim 34 wherein the cation is selected from the group consisting of calcium, copper, barium, magnesium, zinc, and iron.

36. The process of claim 35 wherein the cation is calcium.

37. The process of claim 29, wherein the upper limit of the MW of the pectin is 140,000.

38. The process of claim 29, wherein the upper limit of the MW of the pectin is 85,000.

39. The process of claim 29, wherein the lower limit of the MW of the pectin is 5,000.

40. The process of claim 29, wherein the lower limit of the MW of the pectin is 20,000.

41. The process of claim 29, wherein the upper limit of the DE of the calcium sensitive amidated pectin is 50%.

42. The process of claim 29, wherein the upper limit of the DE of the calcium sensitive amidated pectin is 30%.

43. The process of claim 29, wherein the lower limit of the DE of the calcium sensitive amidated pectin is 0%.

44. The process of claim 29, wherein the lower limit of the DE of the calcium sensitive amidated pectin is 5%.

45. The process of claim 29, wherein the lower limit of the DE of the calcium sensitive amidated pectin is 10%.

46. The process of claim 29, wherein the upper limit of the degree if amidation (DA) of the calcium sensitive amidated pectin is 40%.

47. The process of claim 29, wherein the upper limit of the DA of the calcium sensitive amidated pectin is 25%.

48. The process of claim 29, wherein the upper limit of the DA of the calcium sensitive amidated pectin is 20%.

49. The process of claim 29, wherein the lower limit of the DA of the calcium sensitive amidated pectin is 0%.

50. The process process of claim 29, wherein the lower limit of the DA of the calcium sensitive amidated pectin is 5%.

51. The process of claim 29, wherein the lower limit of the DA of the calcium sensitive amidated pectin is 10%.

52. The process of claim 29, wherein the calcium sensitive pectin is derived from citrus pectin.

53. The process of claim 52, wherein the citrus pectin is selected from the group consisting of lime, lemon, grapefruit, and orange.

54. A pectin fiber prepared by the process of claim 29.

55. The pectin fibers of claim 54 are soft and resilient fibers.

56. The process of claim 29 wherein the coagulation bath is acidified to a pH of between 2 to 3 for fibers spun using a low DE pectin in the composition to produce fibers with a soft silky hand feel.

57. The process of claim 29 wherein the coagulation bath is acidified to a pH of between 4 to 6 to produce fibers with high levels of tensile strength.

58. A wound dressing composition for topical medical application to a wound comprising a gauze material that can be loosely woven or non woven prepared from the pectin fibers of claim 1.

59. A wound dressing composition for topical medical application to a wound comprising a gauze material that can be loosely woven or non woven prepared from the pectin fibers of claim 54.

60. The wound dressing composition of claim 58 wherein an adhesive backing material is present.

61. The wound dressing composition of claim 59 wherein an adhesive backing material is present.

62. The wound dressing composition of claim 58 wherein medicine is present in the dressing.

63. The would dressing composition of claim 59 wherein medicine is present in the dressing.

64. The wound dressing composition of claim 58 wherein medicine is incorporated directly into the pectin fibers.

65. The wound dressing composition of claim 59 wherein medicine is incorporated directly into the pectin fibers.

* * * * *